(12) United States Patent
Jané López

(10) Patent No.: US 12,339,268 B2
(45) Date of Patent: Jun. 24, 2025

(54) DEVICE AND METHOD TO DETERMINE THE QUALITY OF A MEAT PRODUCT

(71) Applicant: FRONTMATEC-AIRA, SOCIEDAD LIMITADA SOCIEDAD UNIPERSONAL, Cardona (ES)

(72) Inventor: Francisco Javier Jané López, Cardona (ES)

(73) Assignee: FRONTMATEC-AIRA, SOCIEDAD LIMITADA SOCIEDAD UNIPERSONAL, Cardona (ES)

( * ) Notice: Subject to any disclaimer, the term of this patent is extended or adjusted under 35 U.S.C. 154(b) by 1182 days.

(21) Appl. No.: 17/051,881

(22) PCT Filed: Apr. 10, 2019

(86) PCT No.: PCT/ES2019/070245
§ 371 (c)(1),
(2) Date: Oct. 30, 2020

(87) PCT Pub. No.: WO2019/211499
PCT Pub. Date: Nov. 7, 2019

(65) Prior Publication Data
US 2021/0190751 A1    Jun. 24, 2021

(30) Foreign Application Priority Data

May 4, 2018   (ES) ................ ES201830436

(51) Int. Cl.
*G01N 33/12*      (2006.01)
*A61M 5/46*       (2006.01)
(52) U.S. Cl.
CPC ............... *G01N 33/12* (2013.01); *A61M 5/46* (2013.01)

(58) Field of Classification Search
CPC ........ G01N 33/12; G01N 33/00; G01N 33/02; A61M 5/46
See application file for complete search history.

(56) References Cited

FOREIGN PATENT DOCUMENTS

ES      1026055 U   * 10/1993   ............. G01N 33/12
ES      1026055       1/1994
(Continued)

OTHER PUBLICATIONS

English Machine Translation of FR1465697 (Year: 1967).*
(Continued)

*Primary Examiner* — Gurpreet Kaur
(74) *Attorney, Agent, or Firm* — Leason Ellis LLP

(57) ABSTRACT

Device and method to determine the quality of a meat product comprising an identifying element that identifies said meat product by means of the emission and/or reception of an identifying signal of the meat product, said identifying signal comprises at least predetermined puncture requirements and/or a puncture depth ($z_i$) in the meat product, positioning means configured to displace a head, where said head is disposed at one end of said positioning means, and comprises an insertion element configured to be inserted inside said meat product at a predetermined puncture depth ($z_i$), and measure at least a pH signal in a predetermined measurement point ($x_i$, $y_i$, $z_i$), the puncture point ($x_i$, $y_i$) being predetermined in accordance with a prior analysis of the anatomy of said meat product by means of an artificial vision device that determines the puncture point ($x_i$, $y_i$) in accordance with the predetermined puncture requirements and anatomy of the meat product.

18 Claims, 7 Drawing Sheets

(56) References Cited

FOREIGN PATENT DOCUMENTS

| ES | 1030953 | | | 11/1995 | |
|----|---------|---|---|---------|---|
| FR | 1465697 | A | * | 1/1967 | ............ F04B 43/067 |
| WO | 2017097684 | | | 6/2017 | |

OTHER PUBLICATIONS

English Machine Translation of ES1026055U (Year: 1993).*
International Search Report issued in PCT/ES2019/070245, mailed Feb. 21, 2020.

* cited by examiner

DEVICE AND METHOD TO DETERMINE THE QUALITY OF A MEAT PRODUCT

CROSS-REFERENCE TO RELATED PATENT APPLICATIONS

This is a U.S. National Phase Application under 35 U.S.C. § 371 of International Patent Application No. PCT/ES2019/070245, filed Apr. 10, 2019, and claims priority to P201830436, filed May 4, 2018, which is incorporated by reference in its entirety. The International Application was published on Nov. 7, 2019, as International Publication No. WO 2019/211499 A2.

The present invention relates to a device to determine the quality of a meat product. It also relates to a method to determine the quality of a meat product by means of the device object of the invention.

BACKGROUND OF THE INVENTION

The determination of the quality of a meat product is a key factor for later processing, since depending on this the product shall be used for one type of processing or another. For example, a leg of pork with a low quality shall be suitable for the production of low-quality cooked ham, and a leg with high quality shall be suitable for salting and drying and obtaining high-quality cured ham.

Different devices and methods are known in the state of the art to determine the quality of a meat product. A first type of devices and methods are based on analysing, by means of, for example, an operator or a colorimeter, the colour of the meat product and classify it by means of a table wherein determined product colours are associated with determined product qualities. This method has the drawback that the operator's subjectivity may affect product classification. Likewise, the lighting conditions of the product, such as the type of light used and the power of light to which said products are exposed may significantly affect product quality determination. Likewise, the product colour varies from when the animal is sacrificed to when it is classified, making it compulsory that quality determination is performed at a certain time after sacrifice of the animal. Furthermore, should the animal suffer a hematoma, due to a bump, the product colour may be affected, causing an error in its classification.

A second type of existing devices is based on the insertion of an element for analysing meat, such as, for example, document EP1093581, where the prediction device comprises a probe which is inserted in a portion of meat, so that it allows a light beam to circulate inside the portion of meat to analyse it. The spectral optical data obtained by means of circulation of the light beam are combined with information from the animal, such as: breed, age, animal category, weight, structure, fattening, pH, meat colour, skin thickness, among others, to determine the quality of the meat product. However, this type of devices have the drawback that to determine meat product quality there must be a large quantity of prior information on the sacrificed animal to combine it with the data that will be obtained by means of the device. Likewise, the device described is mainly designed to be used by an operator so that the accuracy of the determination of the product quality shall depend, in large part, on the operator's expertise in handling said device, since the quality determination may vary significantly depending on the point of the meat product where the puncture is performed.

Other types of methods known are based on the pH measurement of the meat product, 24 hours after sacrifice of the animal, the time wherein the value of said pH of the animal sacrificed is stabilized. This pH value is determined by a scale which measures the degree of acidity of an object. This scale comprises values that range from 0, the most acid value, to 14, the most alkaline value. A decrease in the pH values from 5.0 to 4.0 means an increase in acidity ten times higher, so that an erroneous measurement of the pH may considerably vary the determination of the meat product quality.

This last type of methods are carried out by means of a probe which is inserted inside the meat product where a pH value is measured. Nevertheless, they have the drawback that the data is not always correct, since the probe is not positioned at a determined position and depth. Additionally, during measurement of the pH, the probe moves from the measurement point giving erroneous pH data. By way of example, the pH range to consider that a leg of pork is high quality and may be suitable to be salted and dried is a pH between 5.7 and 5.85, which means the pH value must be extremely precise.

The need is, therefore, clear of having a device and method that allows determining the quality of meat products quickly and guaranteeing total accuracy of the pH value measured, optimizing the selection process of the meat products for their later processing.

DESCRIPTION OF THE INVENTION

The objective of the present invention is to resolve the mentioned drawbacks by developing a device and a method to determine the quality of a meat product.

In accordance with this objective, according to a first aspect, the present invention relates to a device comprising an identifying element that identifies the meat product by means of the emission and/or reception of an identifying signal of the meat product, said identifying signal comprises at least predetermined puncture requirements and/or a puncture depth ($z_i$) in the meat product. This device further comprises positioning means configured to displace a head that is disposed at one end of the positioning means, and comprises an insertion element configured to be inserted inside the meat product to a predetermined depth ($z_i$), and measure at least a pH signal of said meat product in a predetermined measurement point ($x_i$, $y_i$, $z_i$), the puncture point ($x_i$, $y_i$) being predetermined in accordance with a prior analysis of the anatomy of said meat product by means of an artificial vision device that determines the puncture point ($x_i$, $y_i$) in accordance with the predetermined puncture requirements and anatomy of the meat product.

According to the same objective, in accordance with a second aspect, the present invention relates to a method to determine the quality of a meat product, by means of the device claimed comprising the stages of:
 a) identifying the meat product by means of an identifying element that emits or receives an identifying signal of the meat product,
 b) displacing, by means of positioning means, the head from a resting position to a predetermined puncture point ($x_i$, $y_i$) in accordance with the predetermined puncture requirements and puncture depth ($z_i$) comprised in the identifying signal of the meat product,
 c) inserting, by means of actuation means, the insertion element inside the meat product to the predetermined the puncture depth ($z_i$) in accordance with the predetermined puncture requirements and puncture depth ($z_i$) comprised in the identifying signal of the meat product, d) maintaining the insertion element in the predetermined measurement point ($x_i$, $y_i$, $z_i$) of the meat product for a predetermined puncture time, to measure at least a pH signal of the meat product, e) transmitting, by means of transmission means, at least the pH signal of the meat product in a measurement point ($x_i$, $y_i$, $z_i$) to a data structure and/or to the identifying element, f) extracting, by means of the actuation means, the insertion element from inside the meat product, and g) displacing, by means of positioning means, the head from a puncture point ($x_i$, $y_i$) to a resting position.

In the present invention, the term meat product shall be understood as, preferably, a meat from an animal, e.g. pork. However, said meat product may be meat selected from beef, ox, horse, ostrich, chicken, duck, goose, quail, partridge, turkey, rabbit, sheep, lamb and goat.

The term data structure shall be understood to be a particular manner of organizing data in a computer so that it can be used efficiently. In the device object of the invention, said data structure is a database comprising values such as the breed, age, animal category, weight, structure, fattening, pH, meat colour, skin thickness, injected fat, among others, so that said database can be consulted and edited. According to a preferred embodiment, said data structure is accessible by means of an identifying element, for example a chip, situated in the meat product.

Preferably, the predetermined puncture requirements and/or puncture depth are determined by the product client, i.e. the one in charge of performing the post-treatment of the meat product, so that the data obtained by means of the puncture can be consulted and verified a posteriori. However, said predetermined puncture requirements and/or puncture depth can be determined, for example, by the ministry of health or quality of the country where said meat product should be consumed.

In the present invention, thanks to the fact that the insertion element displaces to be positioned in a predetermined puncture point where it is inserted in the meat product and measures at least the value of its pH, it is possible to satisfactorily determine the quality of said meat product with high precision and reliability. The present invention manages to position with high precision, the insertion element in a determined measurement point and maintain it during the determined time the measurement operation lasts.

A fast, simple and totally reliable device and method is thus obtained to determine the quality of a meat product. Likewise, the degree of precision of the classification for the later processing of meat products according to their quality enormously improves on performing the puncture in a determined puncture point ($x_i$, $y_i$) and during a determined time. Furthermore, the device claimed may allow determining the quality of a meat product automatically, without the intervention of an operator.

Below, embodiments of the device and method are described according to the dependent claims described below.

Preferably, the positioning means comprise, for example a robot with six degrees of freedom and, are configured, in addition to being positioned in a predetermined puncture point ($x_i$, $y_i$), to be able to move in a synchronized manner with transport means of the meat product, so that during the puncture time the insertion element is inserted in a predetermined puncture depth ($z_i$) in the meat product.

In this way, the device head may move in a three-dimensional space in any direction and perform any type of rotation. Likewise, the head may displace with the insertion element inserted inside the meat product, without the interruption of the meat product displacement in, for example, the production chain.

Again preferably, the head comprises actuation means, for example a piston with buffer, configured to insert the insertion element inside the meat product to a predetermined puncture depth ($z_i$). In this way, the insertion element is introduced in the meat product to reach a predetermined puncture depth ($z_i$), and the piston buffer guarantees that at least the pH of the meat product is performed right in the predetermined measurement point ($x_i$, $y_i$, $z_i$) without it being able to move.

According to a preferred embodiment, the insertion element comprises a pH sensor, for example an electrode, configured to measure the pH in the measurement point ($x_i$, $y_i$, $z_i$) of the meat product. The surface of said sensor reacts with the pH of the measurement point ($x_i$, $y_i$, $z_i$) creating an electric signal. Later, said electric signal can be transmitted by means of an electric or radiofrequency signal to a data structure and/or to the identifying element of the meat product. Additionally, a converter may convert said electric signal to a value of the pH scale for the degree of acidity, with 0 being the most acid and 14 the most alkaline value.

Advantageously, the head further comprises a calibration element of the pH sensor of the insertion element to guarantee correct measurement of the pH. In this way, the pH sensor can be calibrated, to correct possible deviations that may arise with the passage of time between the pH measurements obtained and the pH reference value. For said calibration, calibration solutions are used with substances with a pH reference value that allow detecting and correcting possible deviations in the measurements.

Preferably, the insertion element comprises an end to penetrate in said puncture point ($x_i$, $y_i$) of the meat product. In this way, the insertion element easily penetrates in the meat product avoiding a possible breakage of the insertion element when it penetrates said meat product.

According to a preferred embodiment, the head has a mechanism to detect the breakage of the end of the insertion element. Said mechanism comprises, for example, two optical fibre cables opposite one another and secured, so that they are positioned one on each side of the insertion element interrupting a light beam between both optical fibre cables. In this way, when the end of the insertion cable breaks, the light beam between the optical fibre cables does not interrupt and activates a warning signal.

Advantageously, the device further comprises transmission means of the pH signal obtained by the pH sensor towards a data structure and/or towards the identifying element of the meat product. Said data transmission is performed by means of an electric and/or radiofrequency signal. In this way, the pH signal obtained by the measurement or the pH value already converted is transmitted to a data structure or to the identifying element, so that it can be consulted at any time, preserving product traceability.

With reference to the method, preferably, before the first stage a), the following stages are performed:

a') analysing the anatomy of the meat product by means of an artificial vision device, and a") determining the puncture point ($x_i$, $y_i$) in accordance with the predetermined puncture requirements and/or puncture depth ($z_i$) given by an identifying signal of the meat product.

In this way, the artificial vision device captures an image of each meat product for its later analysis by means of a computer program. In this analysis it determines, bearing in mind the predetermined puncture requirements and/or puncture depth ($z_i$), the exact point of puncture ($x_i$, $y_i$) of each meat product. It must be considered that each meat product may vary in its dimensions and morphology, so that in accordance with the predetermined puncture requirements provided it calculates the exact puncture point ($x_i$, $y_i$). For example, the predetermined puncture requirement may be to measure the pH at 5 cm from the thigh bone of the meat product. Later, said information ($x_i$, $y_i$) can be transmitted to the identifying element. By means of this stage, it combines and automates the data processing of the meat product and the predetermined puncture requirements and/or puncture depth ($z_i$) to obtain the puncture point ($x_i$, $y_i$) in a determined meat product.

Optionally, stage d) includes the stage of:
d1) converting the pH signal of the meat product to a value of the pH scale for the degree of acidity.

In this way, the pH signal, for example in format of electric signal, is converted to a defined value within the pH scale for the degree of acidity.

According to the method claimed, the positioning means are configured, in addition to being positioned in a puncture point ($x_i$, $y_i$), to be able to move in a synchronized manner with transport means of the meat product, so that during the time the puncture lasts said insertion element is removably inserted to a puncture depth ($z_i$) of said meat product. In this way, the meat product does not interrupt its movement, for example, through the production chain, whilst the measurement is taken of at least the pH of the meat product, so that the quality determination operation of the meat product does not entail any added time in the processing stage where the meat product is located.

According to an embodiment of the method, the puncture time is between 4 and 10 seconds, for example 6 seconds. In this way, after these seconds, the pH measurement no longer fluctuates and it is stable, so that it is considered suitable for determining the quality of the meat product.

BRIEF DESCRIPTION OF THE FIGURES

For a better understanding of all the aforementioned, drawings are attached wherein, schematically and only by way of non-limiting example, a practical case of embodiment is represented.

DESCRIPTION OF A PREFERRED EMBODIMENT

A preferred embodiment of the device 1 is described below, making reference to FIGS. 1 to 7.

In said embodiment, the meat product 5 of which the quality is determined is pork half carcass. Likewise, the puncture requirements and the puncture depth are determined by the product client, i.e. the one in charge of performing the post-treatment of the meat product. Likewise, an artificial vision device (not represented) determines, by means of an analysis of the meat product 5, the puncture point (xi, yi) in accordance with the puncture requirements and anatomy of the meat product 5. Said artificial vision device (not represented) includes at least one camera for the capture of images of the meat product 5 and a computer program that analyses said images combining them with the puncture requirements to determine the puncture point (xi, yi). Likewise, the puncture time (t) during which the insertion element 4 is maintained inside the measurement point (xi, yi, zi) of the meat product 5 is six seconds.

It should be highlighted that in the embodiment described, the meat product 5 is in movement at all times, so that the production chain is not affected by the determination of the quality of the meat product 5.

Figure 6:
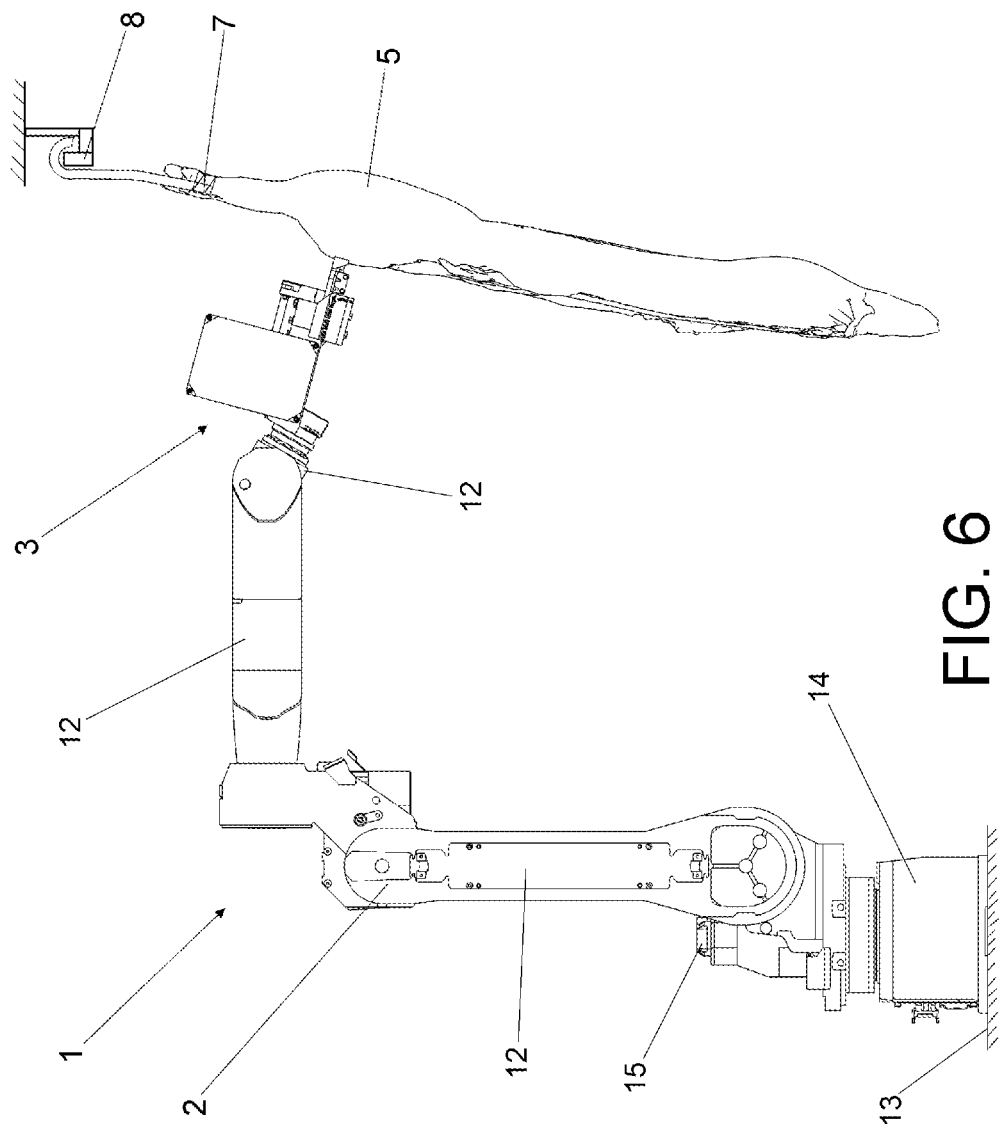
FIG. 6 shows a side elevational view of the device object of the invention when the head is situated in a puncture point (xi, yi) and the insertion element has been actuated by the actuation means to a depth (zi) inside a meat product.
Figure 7:
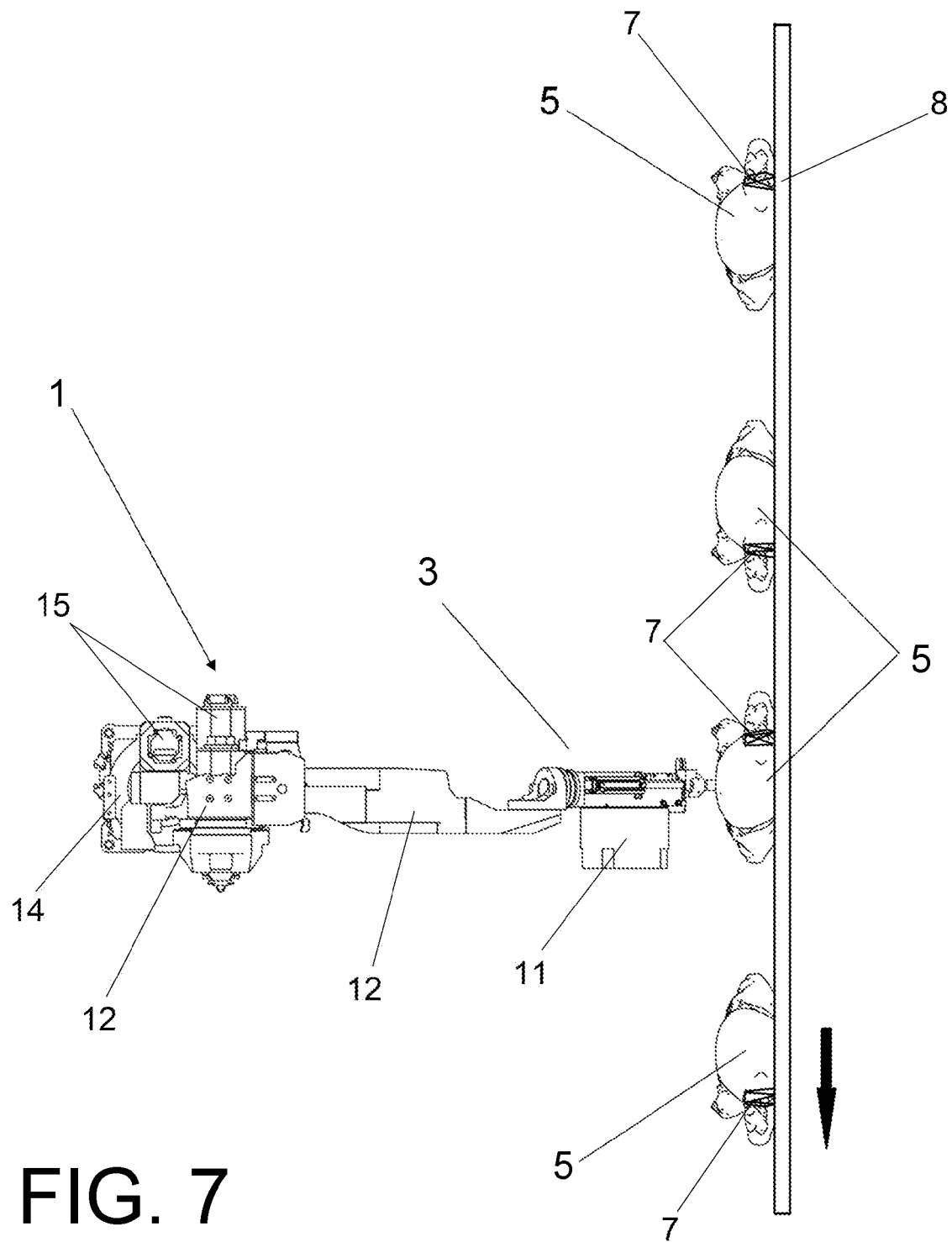
FIG. 7 shows a top elevational view of the device object of the invention in a production chain comprising a plurality of meat products disposed to determine their quality by means of the displacement of the head to a puncture point (xi, yi) and the insertion of the insertion element to a depth (zi) of said meat product.

In the embodiment described, the device 1 is also provided with an identifying element 7, specifically a chip, that identifies said meat product 5 by means of the emission and/or reception of an identifying signal of the meat product 5 (see FIG. 6). This identifying signal comprises at least the puncture requirements and puncture depth (zi) in the meat product 5 determined by the artificial vision device (not represented).

Figure 1:
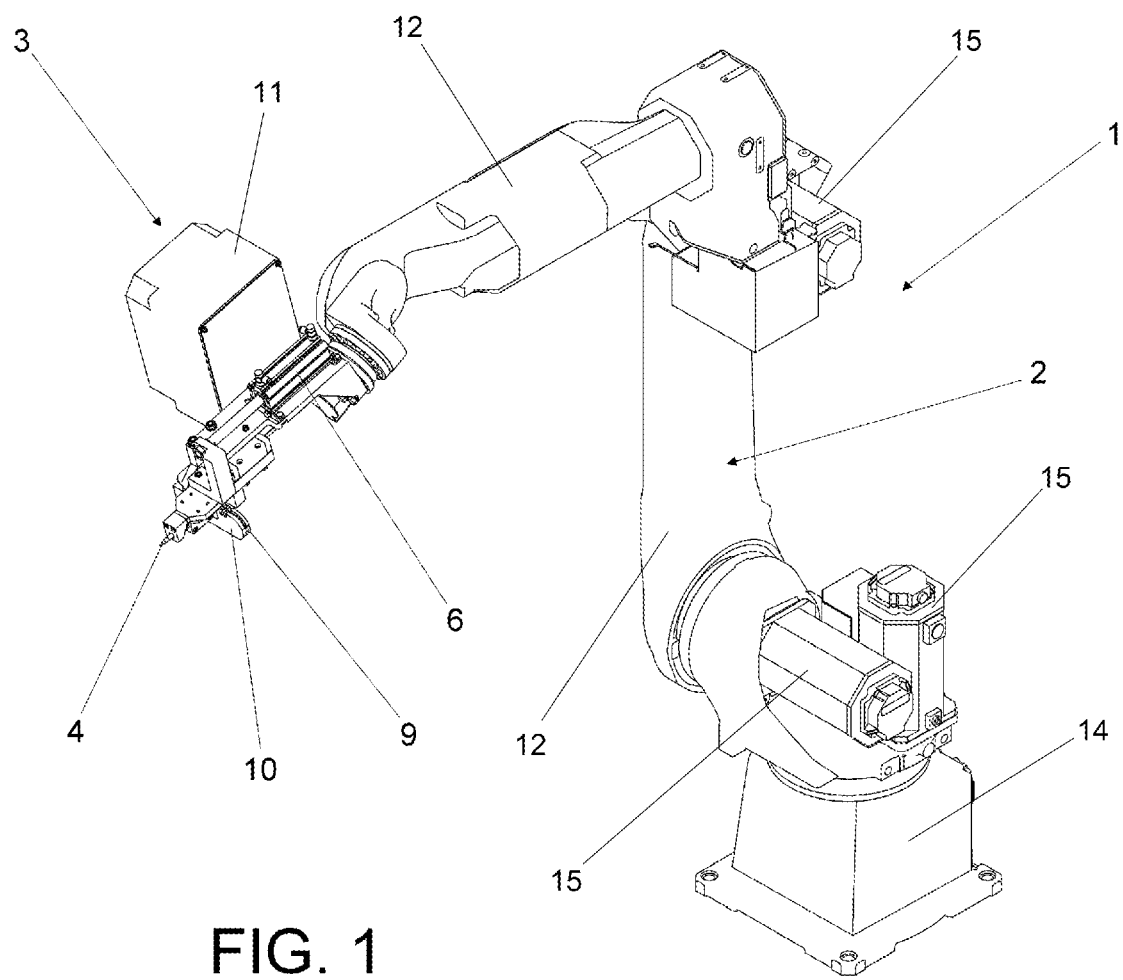
FIG. 1 shows a perspective view of the device object of the invention where the insertion element is situated in a measurement point (xi, yi, zi), with the meat product not being represented.

The device 1 of the present invention comprises positioning means, specifically a robot 2 with six degrees of freedom, capable of displacing a head 3 disposed at one end of an arm 12 of the robot 2 and which has an insertion element 4, and position it at any point in a three-dimensional space (see FIG. 1). Likewise, the robot 2 can displace in a synchronized manner with transport means 8 of the meat product 5.

In the embodiment described, the robot 2 is disposed on a base 14 by way of a bedplate which allows the robot 2 to be seated. Likewise, this base 14 is located on a flat surface 13. The arms 12 of the robot 2 are articulated so that they rotate with respect to axes by the actions of servomotors 15 which allow positioning and displacing the head 3 to the desired positions.

As observed in FIGS. 2, 3, 4 and 5, the head 3 includes an insertion element 4 to penetrate inside the meat product 5 at a determined puncture depth (zi). The insertion element 4 has a pH sensor on its surface with an electrode to measure a pH signal in a determined measurement point (xi, yi, zi) of the meat product 5. Likewise, the insertion element 4 has a sharp end to facilitate penetration inside the meat product 5.

According to an alternative embodiment, not represented, the head 3 includes a calibration element (not represented) of the pH sensor of the insertion element 4 to guarantee correct pH measurement. This calibration element (not represented) is located in the control box 11 together with other elements to guarantee the correct operation of the device, such as, for example, transmission means (not represented).

Figure 2:
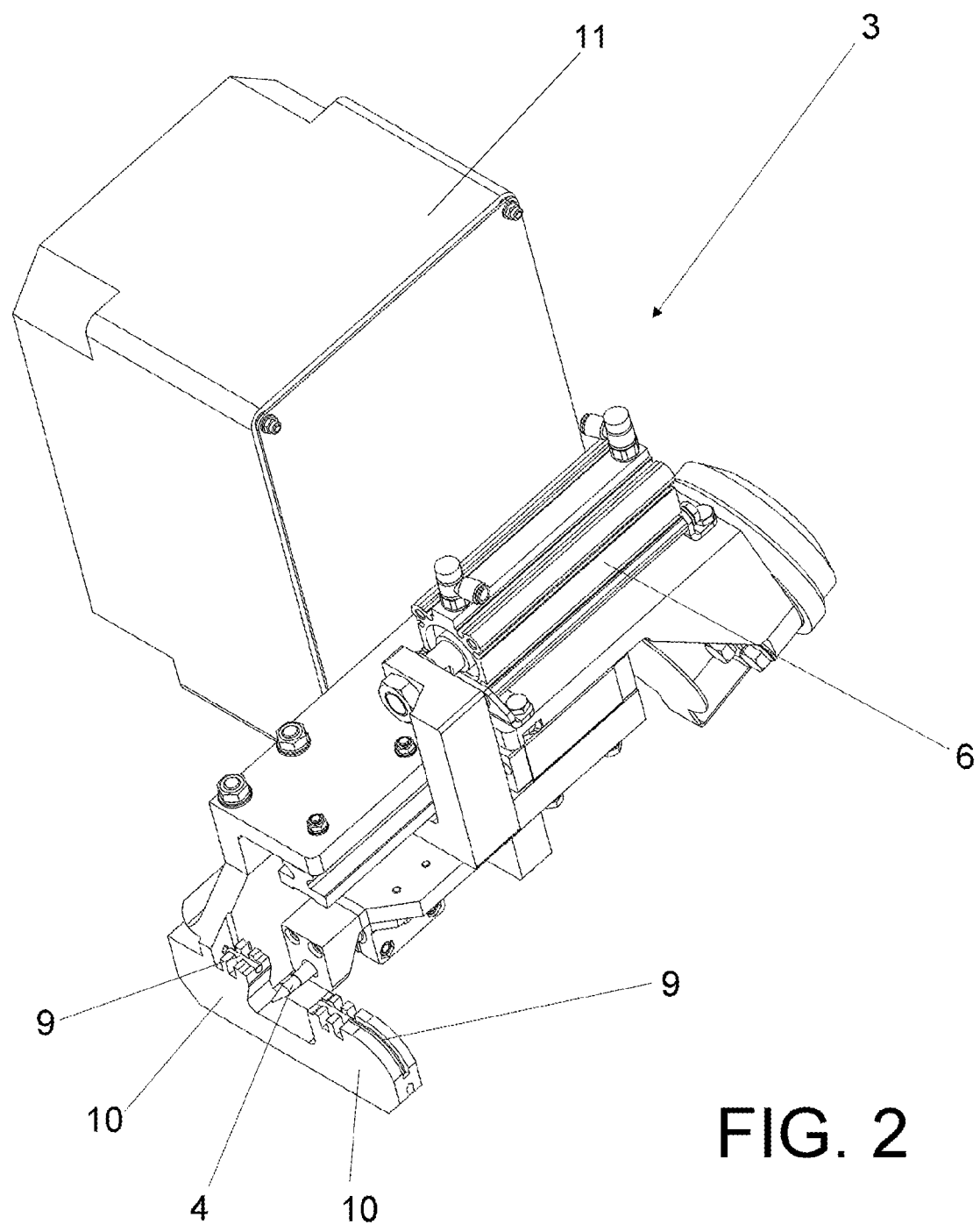
FIG. 2 shows a perspective view of the head of the device object of the invention when the insertion element is not actuated by the actuation means.

As observed in FIG. 2, the head 3 has a mechanism to detect the breakage of the end of said insertion element 4. Said mechanism comprises staples 10, situated in the surrounding area of the insertion element 4, to secure two optical fibre cables 9, opposite one another and located one on each side of the end of the insertion element 4. These optical fibre cables 9 make a light beam circulate which is interrupted by the tip of the insertion element 4. In the event of breakage of the tip of the insertion element 4, the light beam is no longer interrupted, activating a warning signal to change said insertion element 4.

Figure 3:
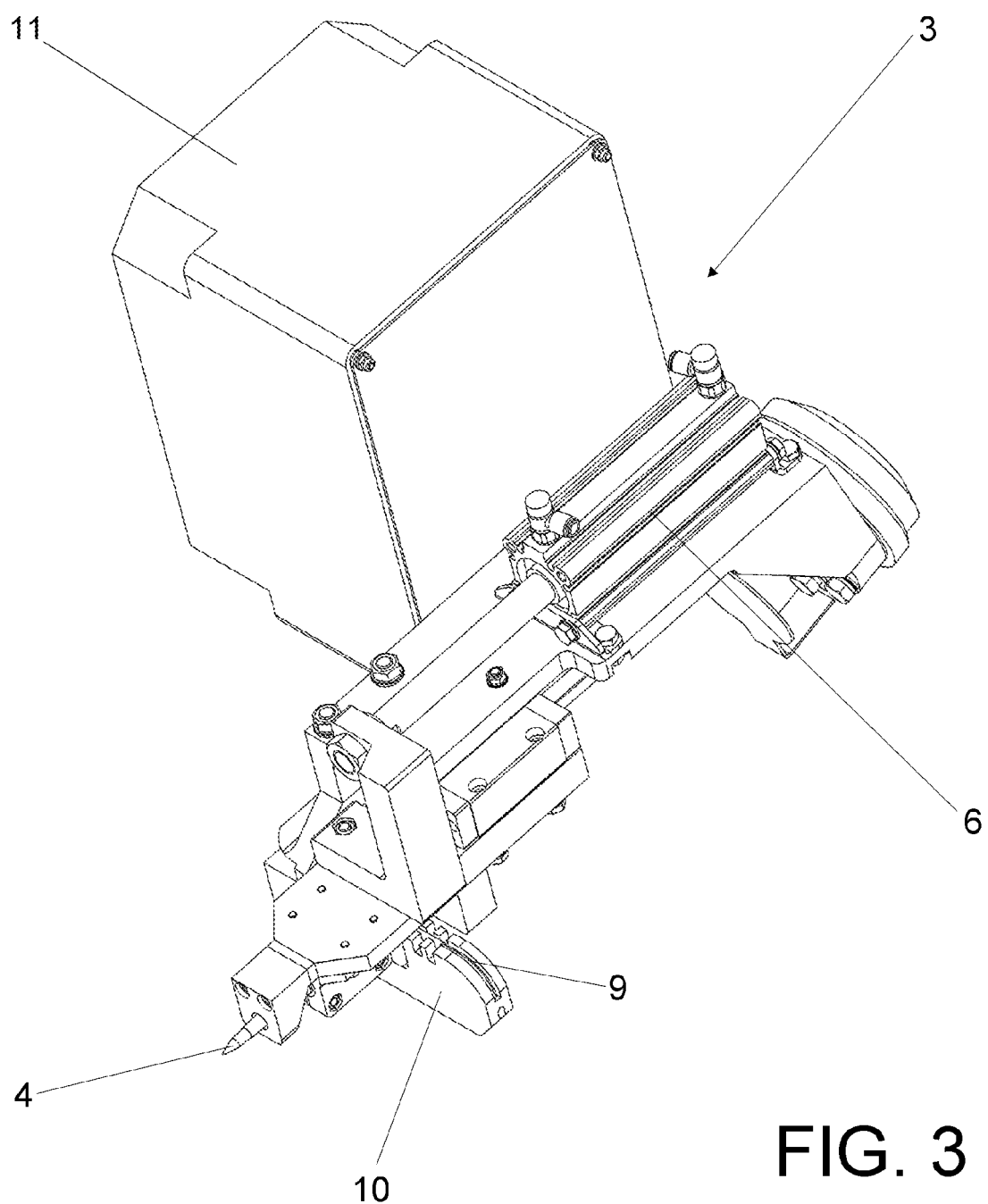
FIG. 3 shows a perspective view of the head of the device object of the invention when the insertion element is actuated by the actuation means.
Figure 4:
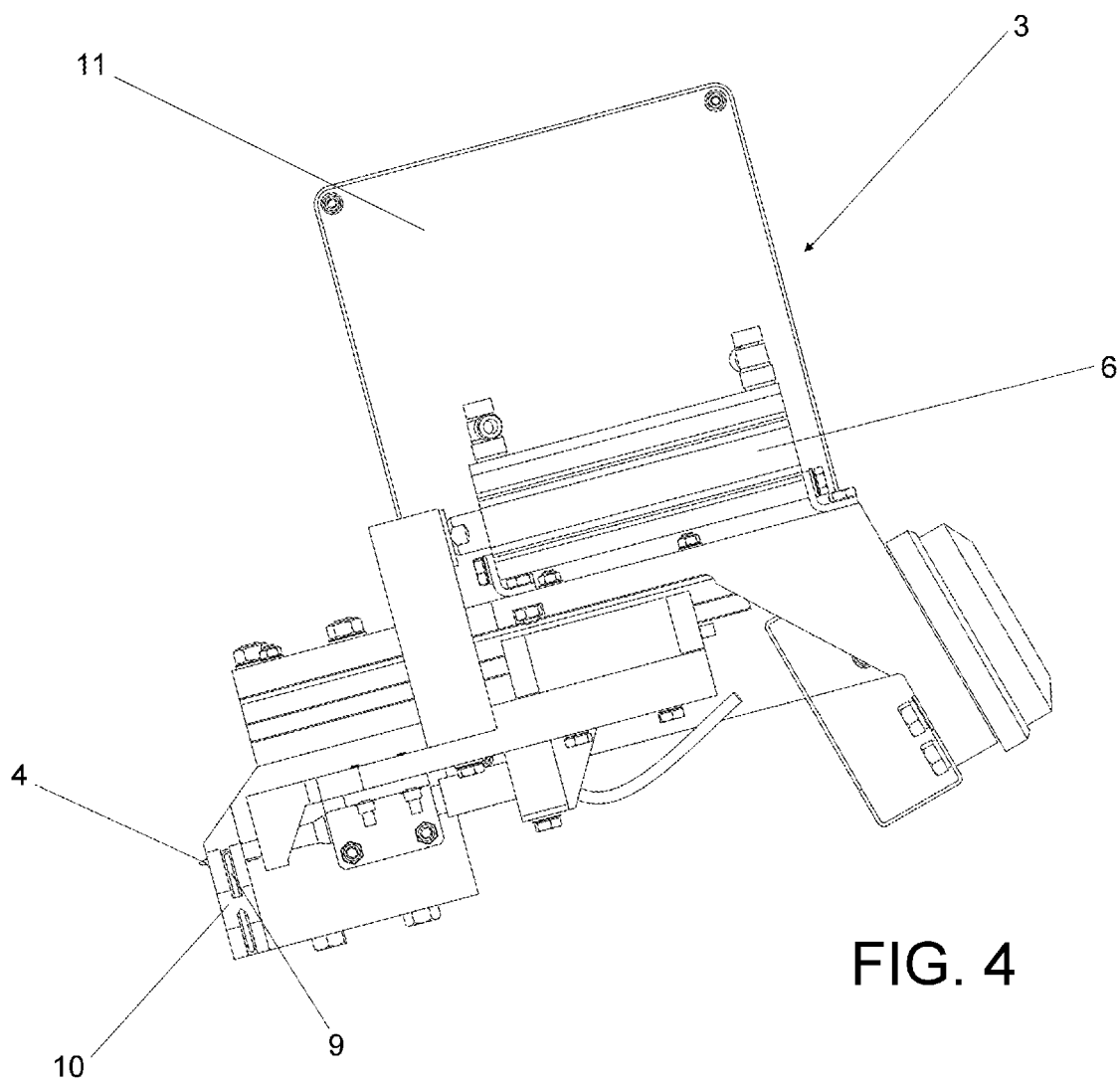
FIG. 4 shows a side elevational view of the head of the device object of the invention when the insertion element is not actuated by the actuation means.
Figure 5:
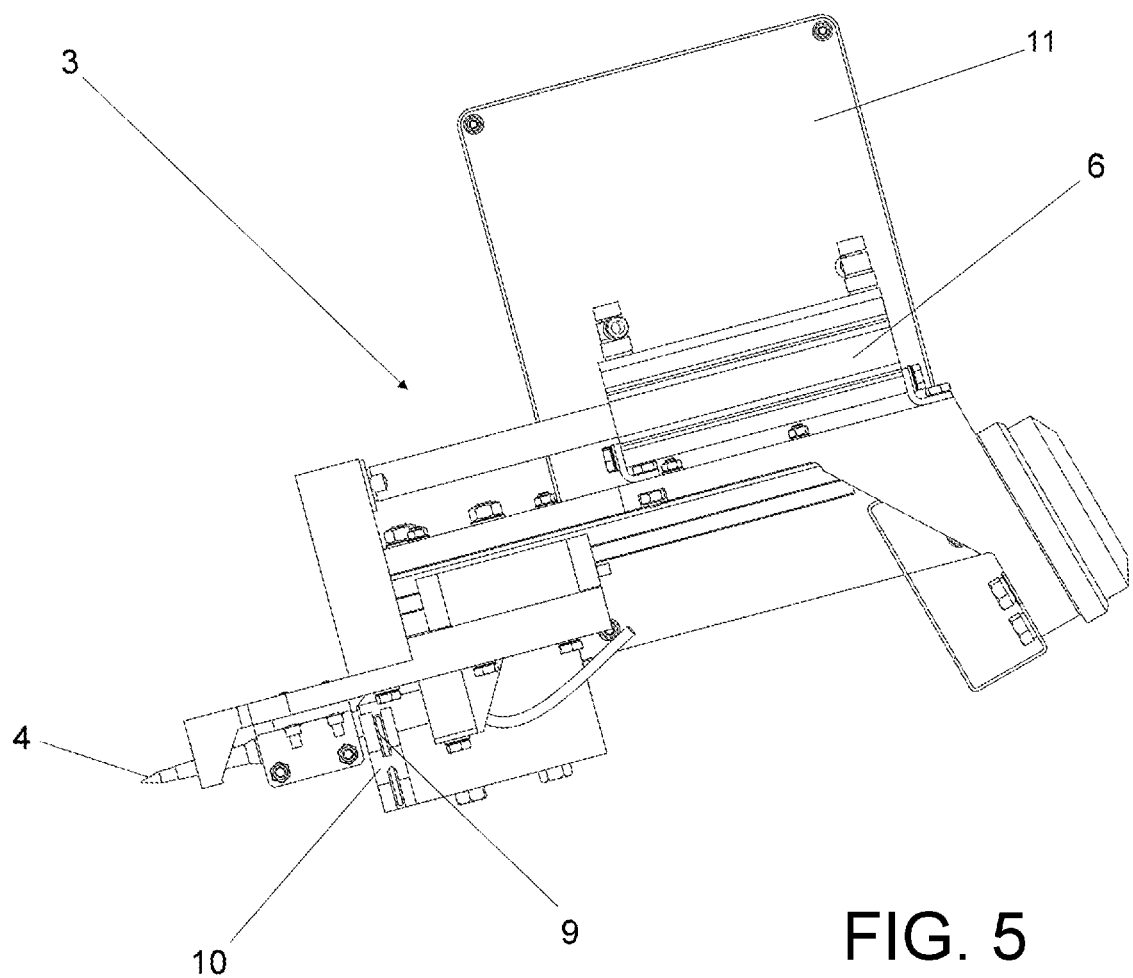
FIG. 5 shows a detailed side elevational view of the head of the device object of the invention when the insertion element is actuated by the actuation means.

In FIGS. 3 and 5, it is observed how the head 3 has actuation means, specifically a piston 6 with buffer configured to displace the insertion element to a predetermined puncture depth (zi), so that said puncture depth (zi) is maintained constant during the puncture time (t) wherein the insertion element 4 is inside the meat product 5.

The device 1 includes transmission means (not represented) which allow transmitting, by means of an electric and/or radiofrequency signal, the pH signal measured by the pH sensor to a database where a multitude of data of each meat product 5 can be consulted and edited. Likewise, the pH signal can also be transmitted to the identifying element 7, so that this is included in the chip of the meat product 5, allowing access to the database information in any phase of the production chain.

The method to determine the quality of a meat product 5 by means of a device 1 of the embodiment described is described below, according to FIGS. 1 to 7.

In a first stage, an artificial vision device (not represented) analyses the anatomy of the meat product 5 and determines the puncture point (xi, yi) in accordance with the predetermined puncture requirements and puncture depth (zi) given by an identifying signal of the meat product (X). Once the puncture point (xi, yi) has been determined, the artificial vision device edits it in a data structure for its later consultation by the device 1 to determine the quality of a meat product 5.

Next, the meat product is displaced, by means of transport means 8 by the production chain to reach the device 1 to determine the quality of a meat product 5 which it identifies by means of an identifying element 7 that emits or receives an identifying signal comprising the puncture point (xi, yi) and the puncture depth (zi) of said meat product 5. Immediately, the robot 2 displaces the head 3 from a resting position to the puncture point (xi, yi) of said meat product.

Once the puncture point (xi, yi) has been situated, the insertion element 4 is inserted in the meat product 5 by means of actuation means 6, specifically a piston with buffer, which allows introducing the insertion element 4 to a depth (zi) comprised in the identifying signal of the identifying element 7.

Simultaneous to the positioning of the head 3 in the puncture point (xi, yi) and to the actuation of the insertion element 4 by the piston 6 with buffer, the robot 2 is displaced synchronized with the meat product 5 to maintain the insertion element 4 inside the meat product 5 for six seconds and to measure a pH signal in the measurement point (xi, yi, zi).

Subsequently, the pH signal of the meat product 5 measured is converted to a value of the pH scale for the degree of acidity and it is transmitted, by means of transmission means, to a data structure and/or to the identifying element 7.

Finally, after the six seconds, the insertion element 4 is removed, by means of the piston with buffer 6, from inside the meat product 5 and the robot 2 displaces the head 3 from a puncture point (xi, yi) to a resting position, where the insertion element awaits to determine the quality of a new meat product 5.

Despite the fact that reference has been made to a specific embodiment of the invention, it is evident for a person skilled in the art that the device and method described are susceptible to numerous variations and modifications and that all the details mentioned can be replaced by other technically equivalent ones, without departing from the scope of protection defined by the attached claims. For example, it has been described that the product to determine the quality of is pork half carcass, this could also be another part of the same animal or an animal selected from beef, ox, horse, ostrich, chicken, duck, goose, quail, partridge, turkey, rabbit, sheep, lamb, goat. Likewise, although it has been described that the puncture requirements and the puncture depth are determined by the product client, they could be determined, for example, by the ministry of health or quality of the country where said meat product should be consumed. Likewise, although it has been described that the puncture time (t) is 6 seconds this could be between 4 and 10 seconds.

The invention claimed is:

1. System to determine the quality of a meat product, characterized in that it comprises:
   an identifying element comprising a chip that identifies each meat product by means of the emission or reception of an identifying signal of the meat product, wherein said identifying signal comprises at least predetermined puncture requirements and/or a puncture depth ($z_i$) in the meat product, and
   a device comprising:
      positioning means configured to displace a head, wherein said positioning means comprise a robot with six degrees of freedom, and
      a head is disposed at one end of said positioning means, and wherein said head comprises an insertion element configured to be inserted inside said meat product at a predetermined puncture depth ($z_i$), and measure at least a pH signal in a predetermined measurement point ($x_i$, $y_i$, $z_i$), a predetermined puncture point ($x_i$, $y_i$) being in accordance with a prior analysis of the anatomy of said meat product (5) by means of an artificial vision device that determines the puncture point ($x_i$, $y_i$) in accordance with the predetermined puncture requirements and anatomy of the meat product and wherein said head comprises a piston with a buffer configured to insert the insertion element inside said meat product to a predetermined puncture depth ($z_i$).

2. System according to claim 1, wherein said positioning means are configured, in addition to being positioned in a puncture point ($x_i$, $y_i$), to be able to displace in a synchronized manner with transport means of the meat product, so that, during the puncture time (t), said insertion element is inserted a puncture depth ($z_i$) of said meat product.

3. System according to any of the preceding claims, wherein said insertion element comprises a pH sensor configured to measure the pH in the measurement point ($x_i$, $y_i$, $z_i$) of the meat product.

4. System according to claim 3, wherein said pH sensor comprises an electrode.

5. System according to any of the preceding claims, wherein said head further comprises a calibration element of the pH sensor of the insertion element to guarantee correct measurement of the pH.

6. System according to claim 1, wherein the robot has arms that are articulated so that they rotate with respect to axes by the action of servomotors which allow positioning and displacing the head to the desired positions.

7. System according to claim 1, wherein the head has a mechanism to detect the breakage of the end of the insertion element, wherein the mechanism to detect the breakage comprises staples, located in in the surrounding area of the insertion element to secure two optical fiber cables, opposite one another and located one on each side of the end of the insertion element, wherein these optical fiber cables make a light beam circulate which is interrupted by the tip of the insertion element, and in the event of breakage of the tip of the insertion element, the light beam is no longer interrupted, activating a warning signal to change said insertion element.

8. System according to claim 1, wherein said insertion element comprises an end to penetrate in said puncture point $(x_i, y_i)$ of the meat product.

9. System according to claim 3, further comprising transmission means of the pH signal obtained by the pH sensor towards a data structure and/or towards the identifying element.

10. System according to claim 9, wherein said transmission means (X) between the insertion element and said data structure and/or towards the identifying element are by means of an electric and/or radiofrequency signal.

11. Method to determine the quality of a meat product by means of a system according to any of claims 1 to 5 and 6 to 10, comprising the stages of:
   a) identifying the meat product by means of an identifying element comprising a chip that emits or receives an identifying signal of said meat product, wherein said identifying signal comprises at least a puncture point $(x_i, y_i)$ or a puncture depth $(z_i)$ predetermined requirements in the meat product,
   b) displacing, by means of positioning means, a head from a resting position to a predetermined puncture point $(x_i, y_i)$ in accordance with the predetermined puncture requirements and puncture depth $(z_i)$ comprised in the identifying signal of the meat product, wherein said positioning means comprises a robot with six degrees of freedom,
   c) inserting, by means of actuation means, an insertion element inside the meat product to the predetermined puncture depth $(z_i)$ in accordance with the predetermined puncture requirements and puncture depth $(z_i)$ comprised in the identifying signal of the meat product,
   d) maintaining said insertion element in the measurement point $(x_i, y_i, z_i)$ of said meat product for a predetermined puncture time $(t_i)$, to measure at least a pH signal of the meat product,
   e) transmitting, by means of transmission means, at least the pH signal of said meat product in a measurement point $(x_i, y_i, z_i)$ to a data structure and/or to the identifying element,
   f) extracting, by means of the actuation means, said insertion element from inside said meat product, and
   g) displacing, by means of positioning means, the head from a puncture point $(x_i, y_i)$ to a resting position.

12. Method according to claim 11, wherein before stage a), the following stages are performed:
   a') analysing the anatomy of said meat product by means of an artificial vision device, and
   a'') determining the puncture point $(x_i, y_i)$ in accordance with predetermined puncture requirements and/or puncture depth $(z_i)$ given by an identifying signal of said meat product.

13. Method according to claim 11, wherein stage d) includes the stage of:
   d1) converting the pH signal of the meat product to a value of the pH scale for the degree of acidity.

14. Method according to claim 12, wherein stage d) includes the stage of:
   d1) converting the pH signal of the meat product to a value of the pH scale for the degree of acidity.

15. Method according to claim 11, wherein said positioning means are configured, in addition to being positioned in a puncture point $(x_i, y_i)$, to be able to displace in a synchronized manner with transport means of the meat product, so that during the puncture time $(t_i)$ said insertion element is removably inserted to a puncture depth $(z_i)$ of said meat product.

16. Method according to claim 11, wherein the puncture time $(t_i)$ is between 4 and 10 seconds.

17. Method according to claim 11, wherein said meat product is a meat of an animal selected from beef, pork, ox, horse, ostrich, chicken, duck, goose, quail, partridge, turkey, rabbit, sheep, lamb, goat.

18. Method according to claim 17, wherein said meat product is a pork half carcass.

* * * * *